United States Patent [19]

Spolyar

[11] Patent Number: 4,630,375
[45] Date of Patent: Dec. 23, 1986

[54] APPARATUS FOR GAUGING AND DETERMINING SPATIAL COORDINATES FOR A SOURCE OF RADIATION TO BE EMPLOYED IN OBTAINING A RADIOGRAPH OF A PATIENT

[76] Inventor: John L. Spolyar, 2769 Homewood Dr., Troy, Mich. 48098

[21] Appl. No.: 729,614

[22] Filed: May 2, 1985

[51] Int. Cl.⁴ .............................................. G01B 11/28
[52] U.S. Cl. ........................................ 33/1 B; 33/512
[58] Field of Search ................. 33/1 C, 1 B, 512, 513, 33/511

[56] References Cited

U.S. PATENT DOCUMENTS

| | | | |
|---|---|---|---|
| 2,557,428 | 6/1951 | Grostic | 33/1 C |
| 3,401,458 | 9/1968 | Mora | 33/1 C |
| 4,131,998 | 1/1979 | Spears | 33/1 C |
| 4,279,259 | 7/1981 | Lee et al. | 33/512 |

*Primary Examiner*—William D. Martin, Jr.
*Attorney, Agent, or Firm*—Lon H. Romanski

[57] ABSTRACT

A template-like gauge has a plate-like body which is at least in most part transparent and carries a reference point and a first plurality of parallel lines along with a read-out portion which in turn is made-up of second and third pluralities of lines to cooperatively define a plurality of gauge areas, each of the gauge areas represents a different set of coordinates for aiming an associated X-ray source; an additional plurality of radiating angularly spaced gauge lines are also provided; when the plate-like body is placed against a lateral cephalogram and the reference point is situated at the articulare and the palatal plane of the cephalogram is positioned at least parallel to one of the lines in the first plurality of parallel lines, the sella appears in one of the gauging areas and the coordinates corresponding thereto are employed for aiming the X-ray source.

7 Claims, 6 Drawing Figures

APPARATUS FOR GAUGING AND DETERMINING SPATIAL COORDINATES FOR A SOURCE OF RADIATION TO BE EMPLOYED IN OBTAINING A RADIOGRAPH OF A PATIENT

FIELD OF THE INVENTION

This invention relates generally to the field of radiography and more particularly to apparatus and method for obtaining the least obstructed radiological exposure of, primarily, the temporo-mandibular joint as in an X-ray image.

BACKGROUND OF THE INVENTION

In many, if not most, procedures involving a person's (patient's) temporo-mandibular joint, it is at least highly desirable, if not totally necessary, to be able to inspect such temporo-mandibular joint by means of an X-ray image. The temporo-mandibular joint (often referred to as the "TMJ") is the articulation of the mandible with the temporal bone component of the cranium.

Such an inspection of the TMJ as by the production of what might be referred to as a standard lateral cephalogram (one that is produced as by the X-ray axis being perpendicular to the mid-sagital plane and the X-ray film being parallel to the mid-sagital plane) is not satisfactory. More particularly, because the juxtaposed co-operating surfaces of the TMJ are not necessarily perpendicular to the mid-sagital plane of the patient's cranium, a standard lateral cephalogram, or the like, taken of such TMJ often produces shadow type or overlapping images, on the X-ray image, which obscures or at least leaves in doubt the true nature or condition of the TMJ being inspected or monitored. Another factor, which not only in itself was a problem but further compounded the problem hereinbefore stated, namely the production of misleading shadows and overlapping images, was that more often than not a patient being treated for any TMJ related problem must have a series of X-ray images taken at selected spaced intervals of time (such may be spaced, for example, in terms of weeks or months) so as to enable the practitioner to observe the effects of the corrective procedures performed on the patient and to determine whether healing is occurring as desired or if further corrective procedures are indicated.

Because such X-ray images are spaced in time, the problem heretofore was one of attempting to position the patient's head, at each succeeding X-ray exposure, as nearly as possible to that position which the patient's head assumed at the immediately preceding X-ray exposure so that in comparing succeeding X-ray images the practitioner could rely upon the observed differences in the compared X-ray images as being a true and accurate indication of the actual changes occurring, during healing, as at the TMJ. However, heretofore, it has not been possible to so orient or position the patient's head, at every succeeding (time-spaced) X-ray exposure as to be assured that the patient's head was actually in the same position (as during the immediately prior X-ray exposure) or at least so close to the same position that the remaining degree of variance would not result in producing misleading X-ray images.

The prior art, in an attempt to avoid taking lateral cephalograms for the continued inspection and monitoring of the TMJ, had started to take the radiographs by aiming the axis of, for example, the source of the X-ray radiation so that such axis passes generally through the patient's cranium and through the TMJ. This, the prior art has done by causing the said axis to be at selected angles posterior and superior to the patient's cranium. However, this has not proven to be successful in that the procedure is one often based on a guess of appropriate aiming of the X-ray axis and the resulting X-ray image may be effectively useless because of interference to the X-ray radiation more often than not caused by the upward extension of the petrous ridge of the petrous bone of the temporal bone. Such bone, and ridge, (one on each side of the mid-sagital plane) extends generally from the side transversely of the cranium and angulates from such side generally forwardly of the cranium. Especially with patients where the prior art had to significantly increase the angular degrees of posterior setting of the X-ray axis, the petrous bone (on the same side as the TMJ being X-rayed) would cause greater and greater interference to the X-ray and produce unwanted images on the resulting X-ray image often causing such X-ray image to be totally useless in determining the then condition of the TMJ. It should be mentioned that the term "posterior" or "posterior setting" means the angle with respect to generally the back of the cranium or with respect to the transporionic axis as viewed from the top of the patient's head. Still another way of defining the "posterior setting" would be to say that it is that angle which the axis of the X-ray appears to make with respect to a plane parallel to the patient's transporionic axis when the back of the patient's head is selectively properly positioned operatively against or with respect to such a plane.

The invention as herein disclosed and described is primarily directed to the solution of the aforementioned and other related and attendant problems of the prior art.

SUMMARY OF THE INVENTION

According to one aspect of the invention, apparatus for gauging and determining the spatial or angular position of the axis of an X-ray source relative to a patient's cranium for purposes of obtaining a least obstructed X-ray exposure of the TMJ in an X-ray image comprises template-like gauge means, wherein said gauge means comprises plate-like body means, said body means at least for the most part being transparent, a reference point designation carried by said body means, a first plurality of generally parallel reference lines spaced from each other and carried by said body means, a read-out portion carried by said body means, said read-out portion comprising a second plurality of generally parallel lines spaced from each other and a third plurality of generally parallel lines spaced from each other, wherein said second plurality of generally parallel lines are so positioned as to be in directions intersecting the directions of the lines of said third plurality of generally parallel lines as to thereby define a plurality of gauge areas generally bound by said second and third plurality of lines, wherein respective ones of said gauge areas represents a different set of preselected angular coordinates for use in positioning the axis of an associated X-ray source, and a fourth plurality of radiating angularly spaced lines, wherein when said plate-like body means is placed against an associated lateral cephalogram and said reference point is situated at the articulare of said cephalogram and the palatal plane of said cephalogram is at least parallel to one of the lines of said first plurality of lines the center of the sella turcica of said cephalogram appears within one of said plurality of gauge areas and the occlusal plane angle of said cephalogram appears within the range of said fourth plurality of radiating angularly spaced lines, said center of the sella turcica by its appearance within said one of said gauge areas determines the corresponding set of angular coordinates for use in positioning the axis of said X-ray source for the next following X-ray exposure.

Various general and specific objects, aspects and advantages of the invention will become apparent when reference is made to the following detailed description considered in conjunction with the accompanying drawings.

BRIEF DESCRIPTION OF THE DRAWINGS

In the drawings wherein for purposes of clarity certain details and/or elements may be omitted from one or more views.

DETAILED DESCRIPTION OF THE PREFERRED EMBODIMENT

Figure 1:
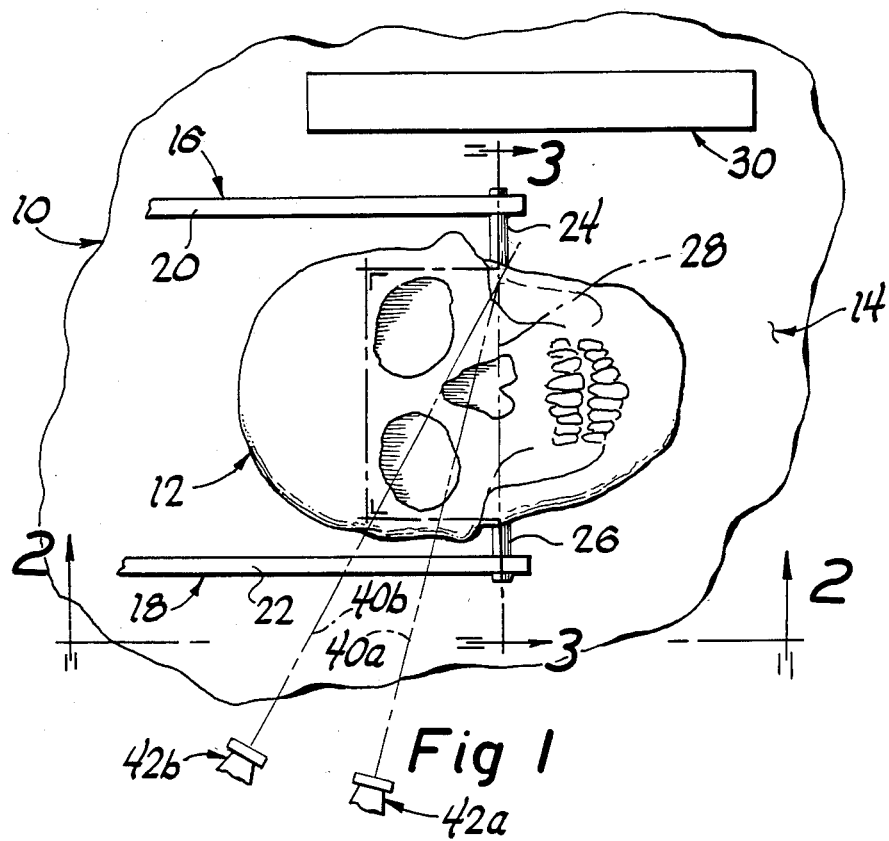
FIG. 1 is a fragmentary view of a patient's head, as represented by a skull, situated within a related appliance and viewed as from above as if the patient were in a generally horizontal reclining position.

Referring now in greater detail to the drawings, FIG. 1 illustrates, fragmentarily and in simplified form, an appliance 10 for referencing to a patient's head, as represented by a skull 12, prior to and during the taking of a radiograph thereof.

The appliance 10, among other things, may comprise suitable base or head back rest and positioning means 14 along with head locating means 16 and 18 which, in turn, may respectively comprise selectively adjustable arm means 20 and 22 and locating members 24 and 26 which are at least partially received within the ears of the patient as to thereby establish the transporionic axis 28. An X-ray film cassette 30 is depicted as being suitably positioned relative to the appliance 10.

Figure 3:
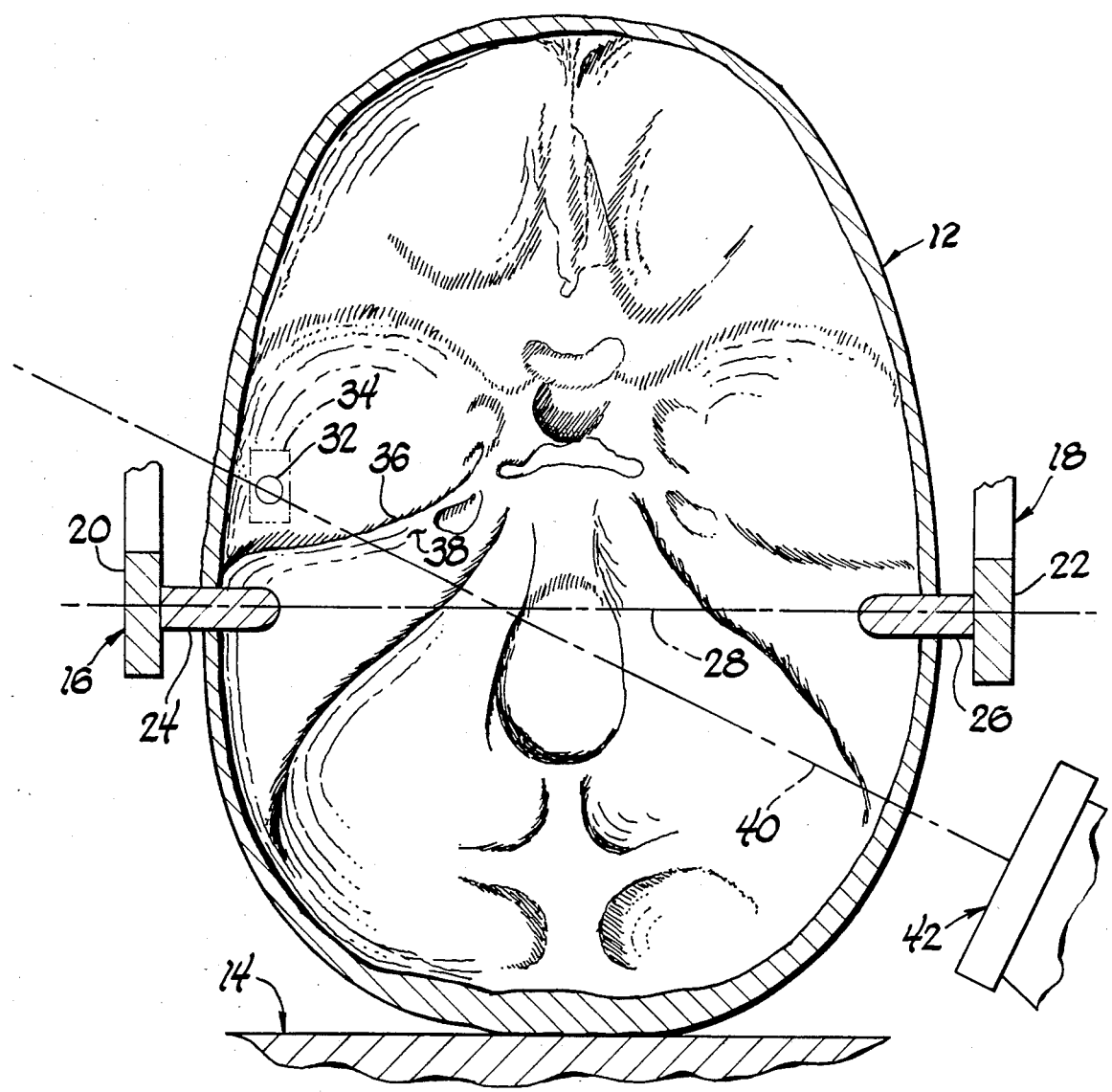
FIG. 3 is a relatively enlarged view, in somewhat simplified form, taken generally on the plane of line 3—3 of FIG. 1 and looking in the direction of the arrows.

Referring in greater detail to FIG. 3, the patient's head (skull) 12, in somewhat simplified form, is depicted as resting with the posterior portion thereof on the head rest or reference plane 14 and with the cap-like portion of such skull removed. The portion of the temporomandibular joint desired to be X-rayed is diagrammatically illustrated by the circle 32 within the general box-like configuration 34. The generally upstanding petrous ridge 36 of the petrous bone 38 of the temporal bone is shown, as is most often the case, in the path of the axis 40 of the X-ray radiation from an associated X-ray source 42 which is depicted at somewhat closer proximity to the skull 12 than as is usual.

Figure 4:
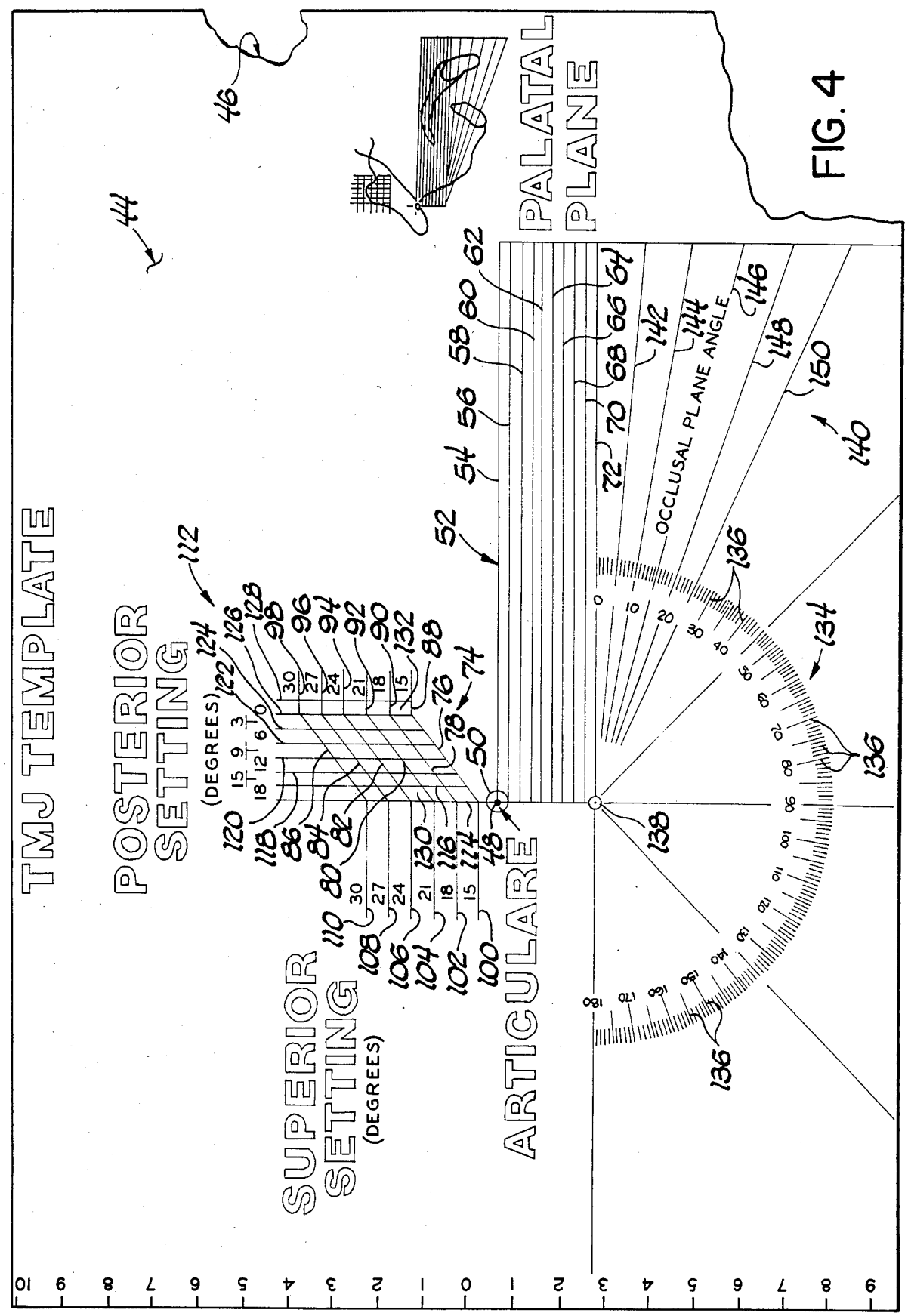
FIG. 4 is a view of gauging apparatus employing teachings of the invention.

FIG. 4 illustrates gauging means 44, employing teachings of the invention, as comprising body means 46 preferably comprised of transparent plastic material such as, for example, Lexan, an acrylic or a polyvinyl chloride. "Lexan" is a trademark of the General Electric Company, of One River Road, Schenectady, N.Y., United States of America, for thermoplastic carbonate-linked polymers produced by reacting bisphenol A and phosgene.

Preferably, a locating or positioning point 48 is located as within a circle 50 and, as will be described, such point 48 and/or circle 50 are employed for placement over or on the articulare of the patient's cephalogram.

The body 46 is also provided with a first plurality 52 of parallel lines comprised as of lines 54, 56, 58, 60, 62, 64, 66, 68, 70 and 72 which are spaced from each other. Although the invention is not so limited, through experimentation, in the preferred embodiment thereof, lines 54–72 are preferably spaced from each other in the order of 2.5 mm. As generally depicted, in the preferred embodiment, line 54 extends from locating point 48 and circle 50. As will be described, such plurality 52 of reference lines are employed with respect to the patient's palatal plane.

Body 46 is further provided with a second plurality of parallel lines 76, 78, 80, 82, 84 and 86 which, at their right ends, as viewed in FIG. 4, are preferably respectively provided with generally horizontally extending line portions 88, 90, 92, 94, 96 and 98. The left ends, as viewed in FIG. 4, of lines 76–86, are also preferably respectively provided with generally horizontally extending line portions 100, 102, 104, 106, 108 and 110 and such are provided mainly for ease of reading the numbers (15, 18, 21, 24, 27 and 30) representing the angular degrees of the superior setting. That is, as can be seen, the numerals "15", "18", "21", "24" and "27" are respectively situated as between: (a) lines 100 and 102 at the left and lines 88 and 90 at the right; (b) lines 102 and 104 at the left and lines 90 and 92 at the right; (c) lines 104 and 106 at the left and lines 92 and 94 at the right; (d) lines 106 and 108 at the left and lines 94 and 96 at the right and (e) lines 108 and 110 at the left and 96 and 98 at the right while numeral "30" is situated immediately above 110, at the left and line 98 at the right.

Additionally, body 46 is provided with a third plurality 112 of parallel lines 114, 116, 118, 120, 122, 124, 126 and 128 which are situated in directions as to intersect the directions of lines 76, 78, 80, 82, 84 and 86. The numbers appearing generally immediately below the heading "Posterior Setting", namely, (read from left to right in FIG. 4) numerals "18", "15", "12", "9", "6", "3" and "0" represent the angular degrees of the posterior setting of the axis of the X-ray source. That is, as can be seen, such numerals are respectively situated effectively as between: (a) lines 114 and 116; (b) lines 116 and 118; (c) lines 118 and 120; (d) lines 120 and 122; (e) lines 122 and 124; (f) lines 124 and 126 and (g) lines 126 and 128.

Such cooperating pluralities 74 and 112 of lines may be considered as a "read-out" portion in that the lines comprising said pluralities 74 and 112, as well as lines 88, 90, 92, 94, 96 and 98, serve to define a plurality of gauging or read-out areas each of which represents a different set of coordinates. In the preferred embodiment, one group of such plurality of gauging areas is typically illustrated by gauging area 130 which has the configuration of a parallelogram. Another group of such plurality of gauging or read-out areas is typically illustrated by gauging area 132 which has the configuration of a right rectangle. Further, a third group of such plurality of gauging or read-out areas exist as above lines 98 and 86 (as viewed in FIG. 4) and respectively between lines 114, 116, 118, 120, 122, 124, 126 and 128.

If, for example, the sella should appear (as will be more fully explained) in the gauging area cooperatively defined by and confined within lines 80, 82, 118 and 120 then this would indicate to the operator of the X-ray machine that the X-ray source should be adjusted so as to have the radiation axis thereof at a superior setting of 21° and at a posterior setting of 12°. If the sella should appear in the gauging area between lines 122 and 124 and above line 86, then this would indicate to the operator of the X-ray machine that the X-ray source should be adjusted so as to have the radiation axis thereof at a superior setting of 30° and a posterior setting of 6°. Further, and still by way of example, if the sella should appear in the gauging area cooperatively defined by and confined within lines 90, 92, 126 and 128 then this would indicate to the operator of the X-ray machine that the X-ray source should be adjusted so as to have the radiation axis thereof at a superior setting of 18° and a posterior setting of 0°.

Through experimentation and testing it has been discovered that in the preferred embodiment of the invention, the first plurality 52 of lines is so constructed as to be perpendicular to line 114 which as depicted, preferably passes through the articulare locating point 48. Further, during such experimentation and testing it has been discovered that in the preferred embodiment the articulare locating point 48 is situated in the order of 5.0 mm. below (as viewed in FIG. 4) the point at which lines 114 and 76 (or the extensions thereof if such were to be the case) intersect.

Also, during experimentation and testing it has been discovered that in the preferred embodiment lines 114, 116, 118, 120, 122, 124, 126 and 128 are preferably spaced from each other in the order of 3.0 mm. while lines 76, 78, 80, 82, 84 and 86 are preferably spaced from each other in the order of 3.8 mm. Such experimentation and testing has also shown that apparently maximum reliability of such a read-out section is obtained if lines 76, 78, 80, 82, 84 and 86, instead of being normal to lines 114, 116, 118, 120, 122, 124 and 126, are situated as to be inclined with respect thereto and, further, that the degree of such inclination with respect to, for example, line 114 is preferably in the order of 51° or, with respect to the lines of the plurality 52, in the order of 39°.

Even though in the preferred embodiment the plurality of gauging or read-out areas hereinbefore described are defined or determined by solid lines, the invention, of course, is not so limited and any suitable means may be employed for delineating or defining respective ones of such a plurality of gauging or read-out areas.

Further, in the preferred embodiment, body means 46 is also provided with a protractor-like portion 134 defining radially extending angularly spaced lines or graduations 136 along with numerical designations of the number of angular degrees represented by selected ones of such graduations. In the preferred embodiment the center 138 of revolution of such protractor-like portion 134 is situated on the extension of line 114 and through experimentation and testing such center 138 is preferably situated at a distance away from articulare locating point 48 in the order of 22.5 mm. Also, preferably, a fourth plurality 140 of angularly spaced lines 142, 144, 146, 148 and 150 are provided in a manner whereby the angles of radiation thereof result in the meeting thereof (if extended) at the center 138. Further, as depicted, said lines 142-150 are relatively elongated and are employed, as will be more fully described, with reference to the patient's occlusal plane angle.

Figure 5:
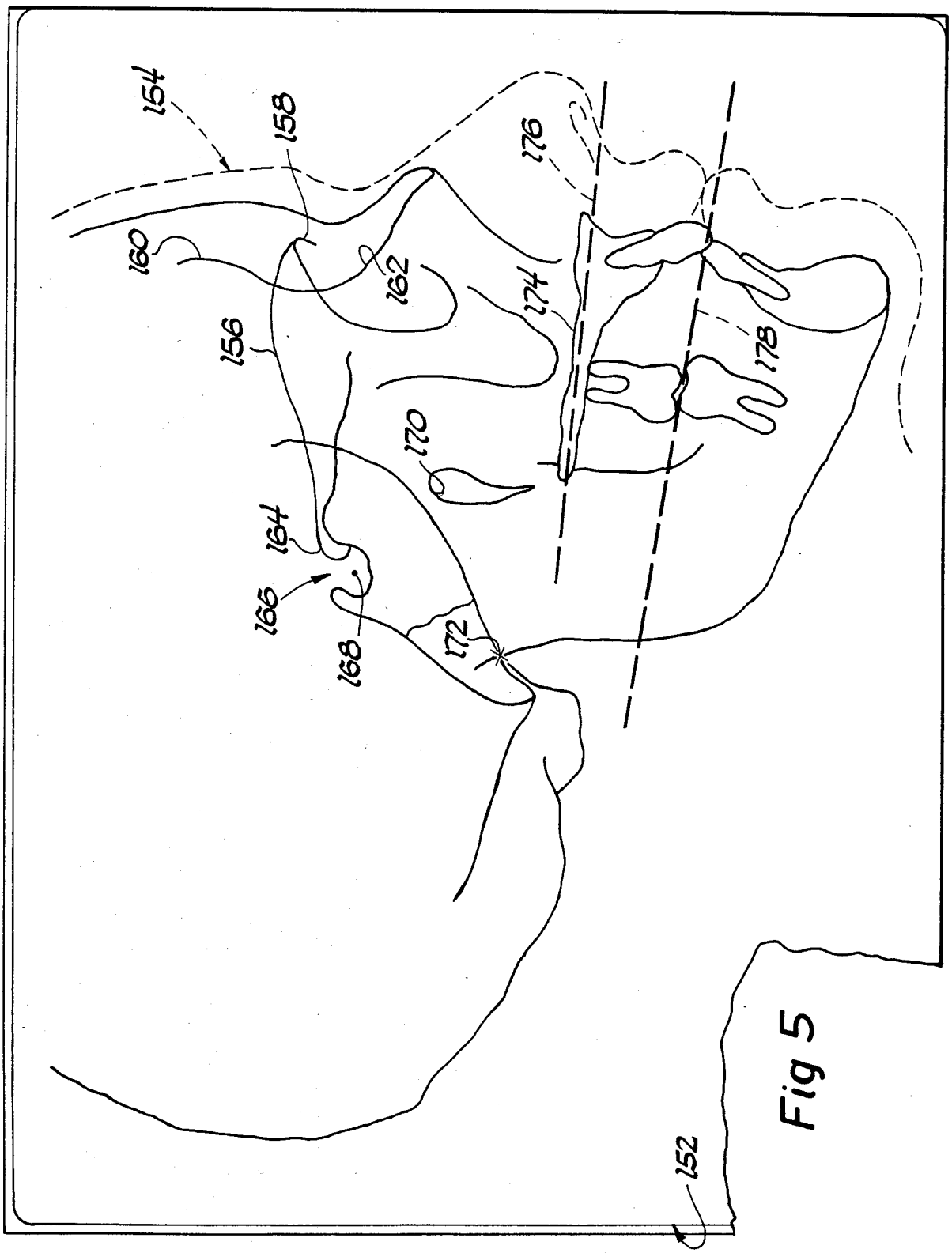
FIG. 5 is a representation of a lateral cephalogram, or a tracing thereof, of a patient.

FIG. 5 depicts, in somewhat simplified form, a lateral cephalogram 152 or tracing thereof of a patient. The hidden line 154 is intended merely to illustrate a portion of the facial tissue even though such would not be visible on the X-ray image. Some of the areas or portions depicted in the cephalogram 152 may be identified as follow: the generally curvilinear line 156 is the orbital plate of frontal and serves as the anterior cranial base; the supraorbital margin is depicted at 158; the frontal crest is shown at 160 and the frontal spine at 162; the anterior clinoid is depicted at 164; the sella turcica is depicted at 166 with the sella (the center of the sella turcica) being depicted at 168; the pterygomaxillary fissure is depicted at 170; the articulare is depicted at 172; the palate is depicted by the generally horizontally extending line 174 of irregular configuration; the palatal plane is depicted by the dash line 176 and the occlusal plane is depicted by the dash line 178. By way of further definition: (a) the articulare is the point where the outline of the ecto-cranial undersurface of the posterior cranial base is crossed by the outline of the back surface of the mandibular ramus; (b) the palatal plane is a line drawn from the most forward point of the palate, anterior nasal spine, to the most posterior point of the palate, posterior nasal spine; (c) the palate is at the same time the anatomic structure which is the floor of the nose and the roof of the mouth and separates these two spaces from each other; and (d) the sella is the centroid of the sella turcica which, in turn, is the anatomic outline of the location of the pituitary gland and represents cephalometrically the confluence of the anterior and posterior cranial bases.

OPERATION OF THE INVENTION

Figure 6:
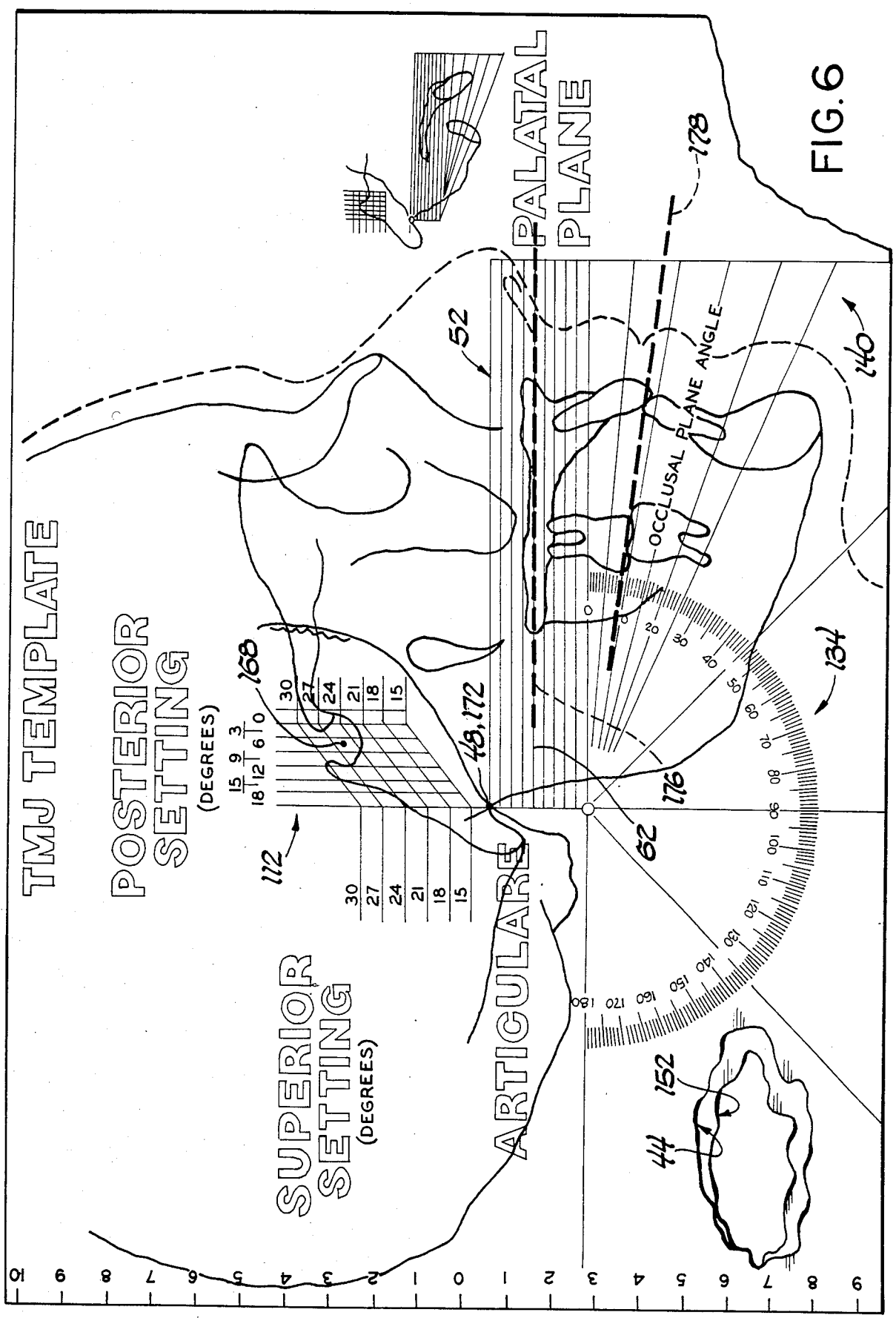
FIG. 6 is a representation of the gauging apparatus of FIG. 4 superimposed as on the cephalogram or tracing of FIG. 5.

The following is presented assuming that it is desired to obtain a TMJ X-ray image of a patient. What would first be done is to obtain a standardized lateral cephalogram of the subject on whom the said TMJ X-ray is desired. Such resulting cephalogram or radiograph, as generally depicted by FIG. 5, is then used in combination with the gauging means of the invention as generally depicted in FIG. 4. More particularly, the gauge or template means 44 is placed upon the FIG. 5 original lateral cephalogram, or tracing thereof, which FIG. 6 is intended to depict. The gauging means or template is first located with respect to the cephalogram 152 in such a manner as to cause the articulare locating point 48 of the gauge or template means 44 to be superimposed upon the articulare 172 of the radiograph (or tracing) 152.

While maintaining such superimposed relationship of points 48 and 172, the operator or practitioner then rotates the gauging or template means 44 until one of the palatal plane lines 54, 56, 58, 60, 62, 64, 66, 68, 70 or 72 of the gauging means 44 either becomes co-linear and superimposed upon the palatal plane 176 of the subject's radiograph or becomes parallel to said subject's palatal plane 176. Once these two relationships are attained, the practitioner then identifies the location of the sella as shown by cephalogram 152 and at the same time determines in which of the plurality of gauging areas such sella appears to be located.

Referring in greater detail to FIG. 6, the gauging means 44 has been placed against the lateral cephalogram 152 and: (a) the articulare locating point 48 has been superimposed on the articulare 172 of the radiograph 152 establishing, in effect, an apparent common point; (b) the gauge means 44 has been rotated and palatal plane line 62 has been found to coincide with the (dash-line represented) palatal plane 176 of the subject; and (c) as a consequence thereof, the sella 168 (FIG. 5) has been found to appear in the gauging area bound by lines 122, 124, 96 and 94 (FIG. 4) thereby indicating that in order to obtain the least obstructed X-ray image of that subject's TMJ, the X-ray source would have to be positioned as to have its axis of radiation with a superior setting of 24° and a posterior setting of 6°. Another reading which is made at this time is the angle of the subject's occlusal plane 178 and such reading may be obtained as from the protractor means 134.

Figure 2:
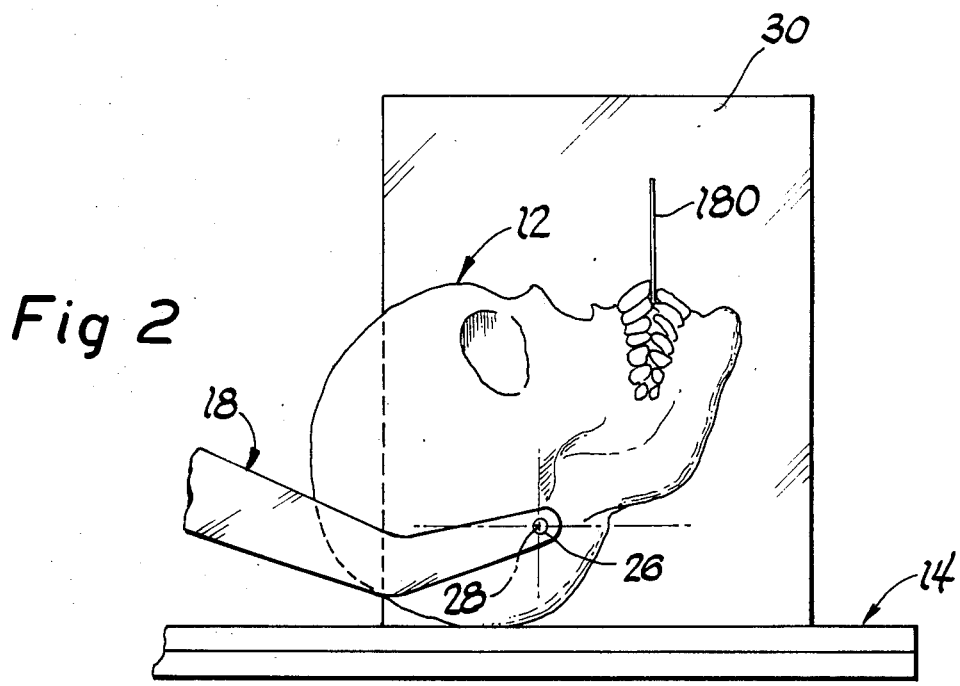
FIG. 2, is a view taken generally on the plane of line 2—2 of FIG. 1 and looking in the direction of the arrows.

Once such readings are obtained, and an X-ray image of the subject's TMJ is to be obtained, the subject may be placed in a reclining position (or any other appropriate position for the then circumstances) as generally depicted in FIGS. 1, 2 and 3, and the subject's head properly located with respect to the locating means 16 and 18. The X-ray source 42, depending upon the superior setting obtained from the gauge area in which the sella appeared, is positioned anywhere from the position depicted at 42a (which would correspond to a 15° superior setting) to the position depicted at 42b (which would correspond to a 30° superior setting). It should be made clear that these two extreme positions depict generally what the X-ray source 42 and the respective radiation axes 40a and 40b would look-like from above as viewed in FIG. 1 even though the X-ray source and resulting axis of radiation may be inclined with respect to, for example, the reference plane 14.

The source of X-ray 42 is then also adjusted to the posterior setting, determined by gauging area in which the sella appeared, and such is generally depicted in FIG. 3. Therefore, if it were assumed that the location of the sella resulted in a superior setting of 30° and a posterior setting of 18°, the source of X-ray and its axis of radiation may appear to have a posterior position as generally depicted in FIG. 3 and a superior position as depicted at 42b of FIG. 1.

Further, before any X-ray exposure is made, the patient is given a plate-like means 180 to bite upon and the angular position of such plate means 180 is then measured to see if it corresponds with the initial occlusal plane angle originally obtained from the superimposition of the gauge means 44 against the lateral cephalogram 152 as described with reference to FIG. 6. If the angle of the plate means 180 does not equal said initial occlusal plane angle, the patient's head is moved, as about the transporionic axis 28, until plate means 180 is at the same angle relative to the vertical (or other operational reference plane) as the said initial measured occlusal plane angle. At this time the patient's head position is stabilized and an X-ray exposure of the patient s TMJ is made.

With such settings recorded it is then possible to take successive (spaced in time) X-ray images of the patient's TMJ merely by again setting the position of the X-ray source to the previously obtained posterior and superior settings and positioning the patient's head as to have the patient's occlusal plane angle as exhibited by the reference or indicator plate 180 match such initially obtained occlusal plane angle.

The gauging means 44 may be of any desired thickness; however, it has been found that a thickness in the order of 1.0 mm. provides for a sufficient rigidity and yet adequate flexibility as to prevent it from being crushed and yet bendable to easily physically conform to a related cephalogram or tracing thereof.

The invention provides an apparatus which assures the production of X-ray images of the TMJ with the least interference from other anatomical structure.

Although only a preferred embodiment of the invention has been disclosed and described it is apparent that other embodiments and modifications of the invention as well as dimensional relationships therein and thereof are possible within the scope of the appended claims.

What is claimed is:

1. Apparatus for gauging and determining the spatial or angular position of the axis of an X-ray source relative to a patient's head for purposes of obtaining a least obstructed X-ray exposure of the patient's TMJ in an X-ray image comprising, template-like gauge means, said gauge means comprising plate-like body means, said body means at least for the most part being transparent, a reference point designation carried by said body means, reference line means carried by said body means, and a read-out portion carried by said body means, said read-out portion comprising a plurality of gauge areas, wherein when said plate-like body means is placed against an associated lateral cephalogram and said reference point is situated at the articulare of said cephalogram and the palatal plane of said cephalogram is positioned at least parallel to said reference line means the sella of the sella turcica of said cephalogram appears within one of said plurality of gauge areas, and wherein said sella by its appearance within said one of said plurality of gauge areas determines a corresponding set of angular coordinates for use in positioning the radiation axis of said X-ray source for the next following X-ray exposure of said TMJ.

2. Apparatus according to claim 1 wherein said reference line means comprises a plurality of parallel reference lines.

3. Apparatus according to claim 1 and further comprising a plurality of radiating angularly spaced lines, and wherein when said plate-like body is so placed against said cephalogram as to have said sella determine said set of coordinates said radiating angularly spaced lines are effective for measuring the occlusal plane angle of said cephalogram.

4. Apparatus according to claim 1 wherein said read-out portion comprises a first plurality of spaced lines and a second plurality of spaced lines, wherein the directions of said spaced lines of said first plurality are such as to intersect the directions of said spaced lines of said second plurality, and wherein said spaced lines of said first and second pluralities by virtue of their intersections cooperate to define said plurality of gauging areas.

5. Apparatus according to claim 1 wherein said plurality of gauging areas comprises a first plurality of gauging areas each having a configuration that of a parallelogram, and a second plurality of gauging areas having a configuration that of a rectangle.

6. Apparatus according to claim 4 wherein said first plurality of spaced lines are parallel to each other and spaced from each other in the order of 3.0 mm., and wherein said second plurality of spaced lines are parallel to each other and spaced from each other in the order of 3.8 mm.

7. Apparatus according to claim 1 wherein said reference line means comprises a first plurality of parallel lines spaced from each other in the order of 2.5 mm., wherein said read-out portion comprises a second plurality of spaced lines and a third plurality of spaced lines, wherein the directions of said spaced lines of said second plurality are such as to intersect the directions of said spaced lines of said third plurality, wherein said spaced lines of said second and third pluralities by virtue of their intersections cooperate to define said plurality of gauging areas, wherein said second plurality of spaced lines are parallel to each other and spaced from each other in the order of 3.0 mm., wherein said third plurality of spaced lines are parallel to each other and spaced from each other in the order of 3.8 mm., and wherein said third plurality of spaced lines are inclined with respect to said first plurality of spaced lines at an angle in the order of 39°.

* * * * *